(12) United States Patent
Krumme

(10) Patent No.: US 7,466,794 B2
(45) Date of Patent: Dec. 16, 2008

(54) MULTI-CHANNEL DATA TRANSMISSION SYSTEM FOR COMPUTER TOMOGRAPHS

(75) Inventor: Nils Krumme, Feldafing (DE)

(73) Assignee: Schleifring und Apparatebau GmbH, Fuerstenfeldbruck (DE)

( * ) Notice: Subject to any disclaimer, the term of this patent is extended or adjusted under 35 U.S.C. 154(b) by 0 days.

(21) Appl. No.: 11/862,575

(22) Filed: Sep. 27, 2007

(65) Prior Publication Data

US 2008/0069146 A1   Mar. 20, 2008

Related U.S. Application Data

(63) Continuation of application No. PCT/EP2005/012375, filed on Nov. 18, 2005.

(51) Int. Cl.
  *G01N 23/00* (2006.01)
(52) U.S. Cl. .......................... 378/19; 378/15
(58) Field of Classification Search ............ 378/4, 378/15, 19
  See application file for complete search history.

(56) References Cited

U.S. PATENT DOCUMENTS

| | | | |
|---|---|---|---|
| 4,646,086 A | 2/1987 | Helzel | |
| 5,134,639 A * | 7/1992 | Vekstein et al. | 378/15 |
| 6,327,327 B1 | 12/2001 | Herold et al. | |
| 6,433,631 B2 | 8/2002 | Pearson, Jr. et al. | |
| 6,650,843 B1 | 11/2003 | Lohr et al. | |

FOREIGN PATENT DOCUMENTS

| | | |
|---|---|---|
| DE | 3215377 | 10/1983 |
| DE | 3331722 | 3/1985 |
| DE | 3400361 | 7/1985 |
| DE | 3530939 | 3/1987 |
| DE | 294829 | 10/1991 |

* cited by examiner

*Primary Examiner*—Jurie Yun
(74) *Attorney, Agent, or Firm*—Kevin L. Daffer; Daffer McDaniel, LLP

(57) ABSTRACT

A device in accordance with the invention for transmitting data between a rotating part and a stationary part of a computer tomograph comprises at least two couplers and receivers connected therewith for receiving signals from a transmission conductor arrangement. Using an evaluation means, a signal is selected from signals received by the receiver on the basis of at least one given quality criterion.

14 Claims, 2 Drawing Sheets

MULTI-CHANNEL DATA TRANSMISSION SYSTEM FOR COMPUTER TOMOGRAPHS

CROSS REFERENCE TO RELATED APPLICATIONS

This application is a continuation of pending International Application No. PCT/EP2005/012375 filed Nov. 18, 2005, which designates the United States and claims priority from German Application No. 10 2005 015 034.9 filed Mar. 31, 2005 (now abandoned), and pending German Application No. 10 2005 027 632.6 filed Jun. 14, 2005.

BACKGROUND OF THE INVENTION

1. Field of the Invention

The invention relates to a data transmission system for transmitting data between the rotating part and the stationary part of a computer tomograph, and to a computer tomograph comprising a corresponding transmission system.

2. Description of the Prior Art

A device for transmitting data in computer tomographs is known from U.S. Pat. No. 6,433,631. A stripline in the rotating part is acted on by the transmission signal. A tap, which is guided at a short distance of the order of approx. 1 mm from the stripline, is provided on the stationary part. This device allows only one data channel (data stream) to be transmitted simultaneously. Furthermore, signal disturbances or signal losses can occur just when the tap is passing through the point of separation between the line and the terminating resistors. This situation is especially critical in differing line lengths such as can occur, for example, owing to manufacturing tolerances.

U.S. Pat. No. 6,327,327 discloses a device comprising a plurality of transmitters and a plurality of receivers for simultaneously transmitting a plurality of signals. A problem in this case is, however, the switching between various sliding contacts or conductors just when the sliding contact is leaving one conductor segment and changing over to the next conductor segment. As soon as the propagation times of the signal through a conductor segment are about one data bit, the signal is distorted, or bits are omitted or else multiply transmitted.

U.S. Pat. No. 6,650,843 discloses an optical transmission device comprising a plurality of transmitters and a plurality of receivers that also has the above-described problem.

BRIEF SUMMARY OF THE INVENTION

The problem of the invention is to propose a data transmission system comprising optionally a plurality of transmitters and/or a plurality of receivers, in which system no data losses or transmission disturbances occur at the points of separation between transmitters and/or receivers.

In accordance with the invention, the above problem is solved by a device for transmitting data between a first part and a second part of a computer tomograph, the parts being rotatable relative to each other, in which the first part comprises: at least one data source; at least one transmission means for receiving data from the data source and transmitting signals; and a transmission conductor arrangement which is fed by the transmission means for guiding the signals along at least a predetermined region of the first part; and the second part comprises: a receiving coupler arrangement for tapping signals from the transmission conductor arrangement; at least one receiving means for receiving signals from the receiving coupler arrangement; a data sink for evaluating or further processing the data supplied by the receiving means; wherein the receiving coupler arrangement includes at least two couplers, at least one coupler being engaged with the transmission conductor arrangement at any moment during a transmission; and wherein the receiving means comprises at least two receivers, each connected to at least one coupler, and also an evaluation means for evaluating signals from the receivers, and the evaluation means selects, on the basis of at least one predetermined quality criterion of the signals from the receivers, the data from at least one receiver for forwarding to the data sink. A computer tomograph comprising said device is further provided herein.

BRIEF DESCRIPTION OF THE DRAWINGS

The invention will be described hereinafter by way of example, without thereby limiting the general idea of the invention, based on embodiments with reference to the drawings, in which.

DETAILED DESCRIPTION OF PREFERRED EMBODIMENTS

Figure 1:
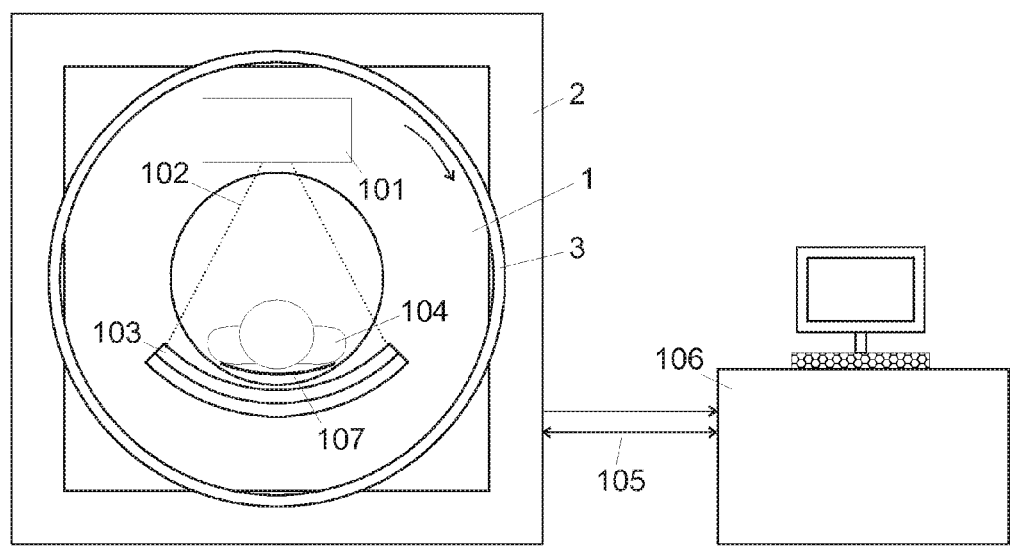
FIG. 1 shows schematically the general form of a computer tomograph.

In accordance with the invention, the above problem is solved by a device for transmitting data between a first part and a second part of a computer tomograph, the parts being rotatable relative to each other, in which the first part comprises: at least one data source; at least one transmission means for receiving data from the data source and transmitting signals; and a transmission conductor arrangement which is fed by the transmission means for guiding the signals along at least a predetermined region of the first part; and the second part comprises: a receiving coupler arrangement for tapping signals from the transmission conductor arrangement; at least one receiving means for receiving signals from the receiving coupler arrangement; a data sink for evaluating or further processing the data supplied by the receiving means; wherein the receiving coupler arrangement includes at least two couplers, at least one coupler being engaged with the transmission conductor arrangement at any moment during a transmission; and wherein the receiving means comprises at least two receivers, each connected to at least one coupler, and also an evaluation means for evaluating signals from the receivers, and the evaluation means selects, on the basis of at least one predetermined quality criterion of the signals from the receivers, the data from at least one receiver for forwarding to the data sink. A computer tomograph comprising said device is further provided herein.

A device according to the invention for transmitting data between the rotating part and the stationary part of a computer tomograph comprises at least one data source on the rotating part and at least one data sink on the stationary part. A data source may, for example, be an X-ray detector or the DAS (data acquisition system) thereof, or else any other control means or computers. A data sink may be a computer for evaluating and processing the data, but also a different control unit.

Also provided in the rotating part is at least a first transmission means and also a transmission conductor arrangement fed thereby. A first transmission means of this type receives data from the data source and converts said data for transmission by the transmission conductor arrangement. The transmission conductor arrangement comprises at least one conductor for guiding electromagnetic waves, which conductor is attached to the rotating part preferably along at least one circular segment or a circular path. The transmission conductor arrangement may, for example, comprise mechanical slip rings, contactless electrical coupling elements, such as inductive or capacitive coupling elements, or else also optical waveguides. The transmission conductor arrangement can also comprise a combination of a plurality of different coupling elements.

Also provided in the stationary part is at least a first receiving means which is fed by a receiving coupler arrangement. The receiving coupler arrangement has at least two couplers, at least one coupler being engaged with the transmission conductor arrangement at any moment during the transmission.

The couplers are configured so as to match the transmission conductor arrangement. Capacitive coupling surfaces may thus, for example, be used in conjunction with a stripline structure as a transmission conductor arrangement. Optical prism couplers in conjunction with an optical waveguides such as, for example, a mirror duct may also be combined as a transmission conductor arrangement.

The receiving means converts the signals received by the receiving coupler arrangement from the transmission conductor arrangement for forwarding to the data sink. The receiving means comprises at least two receivers and also an evaluation means for evaluating the signals from the receivers. An evaluation means evaluates signals from at least one receiver and selects the data from at least one receiver for forwarding to the data sink on the basis of at least one quality criterion. Instead of the selection of the output data from a receiver, signals inside a receiver or else the input signals thereof could also be selected or switched over. In a device for the simultaneous transmission of a plurality of signals (a plurality of channels), a number, corresponding to the number of signals to be transmitted, of signals from the receivers is selected. If, for example, only a single channel is transmitted, only one signal from a receiver will also be selected and forwarded to the data sink.

In addition to a quality criterion, further switching signals, for example position signals or else signals contained in the data stream, can also be used for switching over.

A device according to the invention can be used to transmit optionally a data stream or else a plurality of data streams simultaneously. A data stream can also be divided into a plurality of parallel data streams using a multiplexer in the data source or in the emitting means. The data can be transmitted in the form of individual data packets. Advantageously, the content is coded so as to allow transmission errors within the data packets to be recognized. In a demultiplexer in the receiving means or the data sink, the data can be checked for correct transmission and any data packets transmitted twice can be rejected or missing data packets re-requested.

The device is advantageously configured so as to allow signals to be transmitted at any angle of rotation between the rotor and stator. Alternatively, transmission can be carried out only in specific positions or in specific regions.

Obviously, a transmission device according to the invention can be used not only in computer tomographs but also in other medical diagnosis systems and also in general rotational transmission tasks. It can also be used in general transmission tasks and, in particular, in linearly moving parts.

An especially advantageous embodiment of the invention provides, as at least one quality criterion, optionally an input signal amplitude, a signal-to-noise ratio, a jitter amplitude, a spectral distribution of the signals, a frame error rate, a parity error rate and/or a bit error rate.

For example, there may be selected from a plurality of receivers that receiver having the best quality. Expediently, a hysteresis is also provided to prevent excessively frequent switching-over.

The selection can also be controlled by a plurality of quality criteria. A selection criterion may thus be based on a combination, weighted by defined or dynamically calculated factors, of a plurality of parameters, for example with differing weighting, or even with a time sequence or time-dependent weighting. For example, a first selection decision could be made on the basis of a parameter to be measured rapidly such as a signal amplitude. For optimization, a criterion subject to a relatively long measuring time, such as a bit error rate, could then be added.

In a further embodiment of the invention, the components specific to the transmission medium, such as the transmission means, transmission conductor arrangement, receiving means and receiving coupler arrangement, are configured for transmitting optical signals.

Alternatively, the components specific to the transmission medium, such as the transmission means, transmission conductor arrangement, receiving means and receiving coupler arrangement, can be configured for transmitting electrical signals or else electromagnetic fields and waves.

In a further advantageous embodiment of the invention, the transmission conductor arrangement is divided into a plurality of segments and the receiving coupler arrangement has at least one coupler more than the number of segments of the transmission conductor arrangement. This allows seamless transmission without data losses.

Another embodiment of the invention provides at least one buffer memory for the intermediate storage of received data, which can be used to prevent data losses during transitions or processes of switching over between various receivers. An intermediate memory of this type can be used to store individual bits or else relatively large data packets, as appropriate.

A further embodiment of the invention provides for data received more than once to be deleted.

In a further embodiment, the emitting conductor arrangement is divided into a plurality of segments, the individual segments being fed with signals by the emitting means in such a way that bit clock pulses or frame clock pulses of adjacent segments are optionally almost in phase with one another. This has the advantage that one or more PLLs which are present in receivers do not fall out of synchronization during transitions between segments of the emitting conductor arrangement via individual couplers. The data losses of individual bits or frames can be compensated for by a corresponding buffer memory.

In a further embodiment, a data stream having a relatively low data rate is added to the main data stream by multiplexing. The data stream having a relatively low data rate preferably has a clock rate having an integer ratio to the data rate of the main data stream. The receiver is able to decode the data stream by oversampling and then digitally to correct it. Alternatively, two parallel receiving channels having a differing data rate can also be used.

A computer tomograph according to the invention comprises at least one of the devices for communication specified hereinbefore.

For the sake of simplicity, the present document will refer to a transmission from the rotating part to the fixed part of a computer tomograph. Obviously, a device according to the invention can also be used in the inverted direction of transmission. Equally, a device according to the invention can also be used in other applications for rotational transmission and likewise for the linear transmission of two units moving relative to each other.

The transmission direction here chosen for the sake of illustration is from the rotor to the stator, as this is the most common application. Nevertheless, transmission in the opposite direction or else bi-directionally is also possible.

FIG. 1 shows by way of example a device according to the invention. A computer tomograph (CT scanner) consists of two mechanical main components. A stationary part 2 acts as a base and carrier for the device as a whole, in which base and carrier a rotating part 1 rotates. A patient 104 is positioned on a rest 107 in an opening in the rotating part. An X-ray tube 101 and also a detector 103 arranged opposing said X-ray tube are provided for scanning the patient using X-rays 102. The X-ray tube 101 and detector 103 are rotatably arranged on the rotating part 1. A rotary joint 3 is used for producing an electrical connection between the rotating part 1 and the stationary part 2. In this case, high electrical power for feeding the X-ray tube 101 is transmitted in a direction of the rotating part 1 and, at the same time, raw data of an image is transmitted in an opposite direction. Communication of control information in both directions is provided simultaneously therewith. An evaluation and control unit 106 is used for operating the computer tomograph and for displaying generated images. Communication with the computer tomograph is carried out via a bidirectional connection 105.

Figure 2:
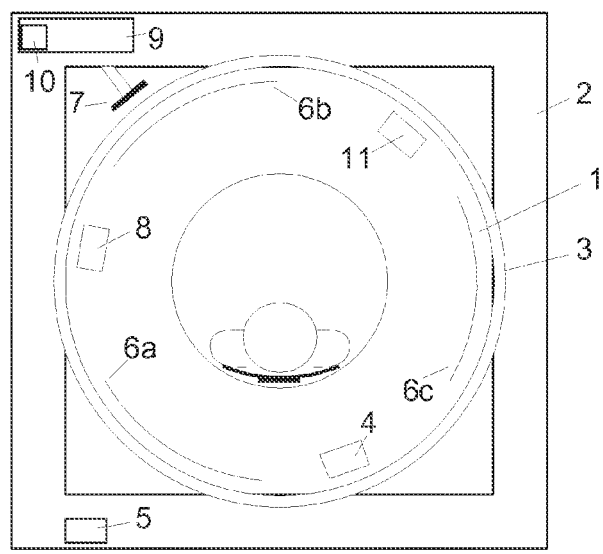
FIG. 2 shows schematically the arrangement of the transmission/receiving means.

FIG. 2 shows in simplified form an exemplary arrangement of a computer tomograph according to the invention comprising components required for transmission. Data from a data source 4 (detector 103 with subsequent signal processing or DAS) on the rotating part 1 is processed using a first transmission means 8 and forwarded to the transmission conductor arrangement which in this case is shown by way of example to consist of three parts 6a, 6b, 6c. This transmission conductor arrangement then guides high-frequency signals. The high-frequency signals are picked off by a receiving coupler arrangement 7. The receiving coupler arrangement shown by way of example is an arrangement which is rigidly connected to the stationary frame. The signals intercepted by this receiving coupler arrangement 7 are forwarded to a first receiving means 9 for processing. The output signals from said receiving means are then guided to a data sink 5.

Figure 3:
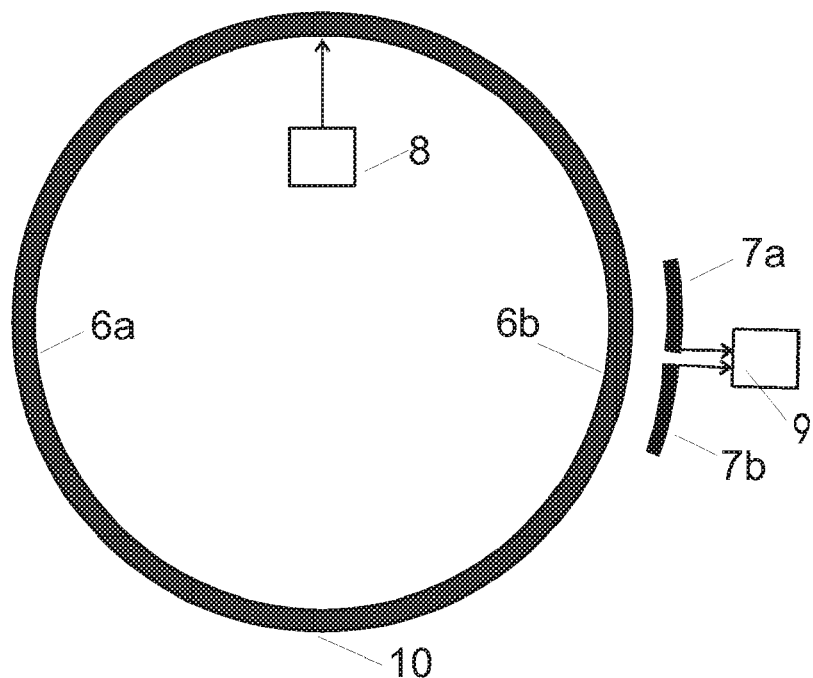
FIG. 3 shows schematically an arrangement with optical transmission.

FIG. 3 shows in simplified form an arrangement with optical transmission. The transmission means 8 is configured as an optical transmission means and feeds optical signals into an optical transmission conductor arrangement 6 consisting of a closed optical transmission conductor. For the sake of clarity, the transmission conductor, which is ideally of one-piece configuration, has been divided into a first half 6a and a second half 6b. Optical signals are fed in at the location of the transmission means 8 and propagate in opposite directions in both halves 6a and 6b. Advantageously, an optical absorber is located at the end position 10. However, an arrangement according to the invention is also able to operate without such an absorber. In this case, it is desirable to use a transmission conductor arrangement with significant attenuation, preferably greater than 6 dB per revolution, particularly advantageously greater than 12 dB per revolution. In this case, therefore, use of the invention allows an inexpensive transmission conductor with relatively high attenuation to be used. The receiving coupler arrangement has two directionally selective receiving couplers 7a and 7b. In the present case, the receiving coupler 7a is configured for receiving signals in the clockwise direction and the receiving coupler 7b for receiving signals in the anticlockwise direction. The signals from these receiving couplers are guided to the receiving means 9 where they are further processed. Advantageously, the signal is chosen from that receiving coupler 7a, 7b having the lowest bit error rate or the lowest frame error rate. A particularly beneficial algorithm is checking for frame or parity errors and switching over to the other receiving coupler as soon as, in one receiving coupler, a specific number of errors has occurred and, in the other receiving coupler, no or fewer errors have occurred at the same time.

The mode of operation of this arrangement will be described based on a circulation of the receiving means comprising receiving couplers along the transmission conductor arrangement, anticlockwise starting from the point of the transmission means 8. At the location of the transmission means 8, both receiving couplers 7a and 7b respectively receive signals of equal strength which propagate, starting from the location of the transmission means 8, toward the two halves 6a and 6b of the transmission conductor arrangement. Which of the two receiving couplers is then selected for issuing the signals depends on the starting conditions of the preceding circulation. If the receiving means then moves anticlockwise away from the location of the transmission means, the second receiving coupler 7b will receive the signal transmitted on the short path from the transmission means 8, whereas the first receiving coupler 7a receives the signal which is transmitted along almost the entire circumference and is therefore markedly attenuated. The second receiving coupler 7b is therefore selected for the signal transmission. At the end position 10, the signals received by both receiving couplers are of equal strength. On further movement, and thus re-approaching the emitting means 8, the first receiving coupler 7a obtains the signal transmitted anticlockwise on the shorter path, whereas the second receiving coupler 7b obtains the signal which is transmitted on the longer path and is therefore more markedly attenuated. The first receiving coupler 7a is then selected. It will be clear that switching-over to the respectively more beneficial receiving coupler is carried out in each case without control by additional position signals.

Figure 4:
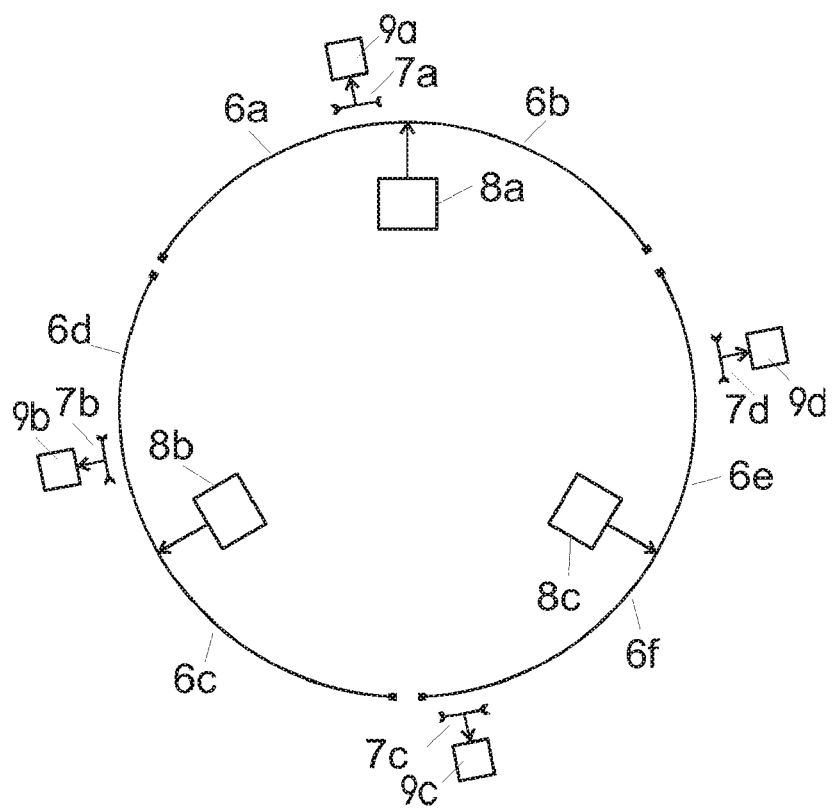
FIG. 4 shows schematically an electrical transmission means.

FIG. 4 shows a further arrangement according to the invention comprising capacitive transmission conductor segments divided into three portions, each portion being divided into two respective segments. In the first portion, the two halves 6a and 6b of the transmission conductor are fed by the transmission means 8a in the center thereof. In the second portion, the two halves 6c and 6d are fed by the transmission means 8b. Finally, in the third portion, the two halves 6e and 6f are also fed by the transmission means 8c. The transmission means 8a, 8b, 8c can also be part of a common transmission means. A signal can also be fed at an end of a transmission conductor part. The transmission conductors are advantageously terminated without reflection. In the present example, they are provided to transmit three different data streams (channels). The four receiving couplers 7a, 7b, 7c, 7d, which are each connected to a receiver 9a, 9b, 9c, 9d, are provided for receiving. The receivers are all rigidly connected to one another and move simultaneously relative to the transmitters. As a result of the fact that there is provided at least one receiver more than the number of transmitters, continuous transmission around the entire circumference is possible even if a receiving coupler is positioned precisely between two transmitting conductor parts, as in this case at least one respective receiving coupler is still engaged with the adjacent transmitting conductor parts. The switching-over of the channel allocation may, for example, be controlled by the signal amplitude in a receiver or else by a bit error rate, as a fall in the signal amplitude and a rise in the bit error rate may be observed in that receiver, or the receiving coupler thereof, which is just passing through the transition between two transmitting conductor segments. Additionally or alternatively, in the data of each channel, a marker of the channel could also be transmitted. In the receiving means, evaluating this information then allows the receivers to be reallocated to the channels.

The size of the data packets (frames) is optimized to the rotational speed, duration of transmission disturbances resulting from an overlap of the aerials, resynchronization time of the PLLs and wave propagation speed on the transmitting aerial, so a disturbance preferably lasts no longer than a packet length. At most two packets are thus disturbed.

The features illustrated in the embodiments may optionally be applied to optical, electrical or other transmission media and are also independent of the number of channels to be transmitted.

The invention claimed is:

1. A device for transmitting data between a first part and a second part of a computer tomograph, the parts being rotatable relative to each other, in which the first part comprises:
   at least one data source;
   at least one transmission means for receiving data from the data source and transmitting signals; and
   a transmission conductor arrangement which is fed by the transmission means for guiding the signals along at least a predetermined region of the first part;
   and the second part comprises:
   a receiving coupler arrangement for tapping signals from the transmission conductor arrangement;
   at least one receiving means for receiving signals from the receiving coupler arrangement;
   a data sink for evaluating or further processing the data supplied by the receiving means;
   wherein the receiving coupler arrangement includes at least two couplers, at least one coupler being engaged with the transmission conductor arrangement at any moment during a transmission; and
   wherein the receiving means comprises at least two receivers, each connected to at least one coupler, and also an evaluation means for evaluating signals from the receivers, and the evaluation means selects, on the basis of at least one predetermined quality criterion of the signals from the receivers, the data from at least one receiver for forwarding to the data sink.

2. The device according to claim 1, wherein the at least one data source is an X-ray detector.

3. The device according to claim 1, wherein the predetermined region of the first part is in the form of at least one circular segment or a circular path.

4. The device according to claim 1, wherein the at least one quality criterion is at least one of an input signal amplitude, a signal-to-noise ratio, a jitter amplitude, a spectral distribution of the signals, a frame error rate, a parity error rate, and a bit error rate.

5. The device according to claim 1, wherein the at least one quality criterion is a combination, weighted by predetermined weighting factors, of a plurality of individual quality criteria comprising at least one of an input signal amplitude, a signal-to-noise ratio, a jitter amplitude, a spectral distribution of the signals, a frame error rate, a parity error rate, and a bit error rate.

6. The device according to claim 1, wherein at least one quality criterion is formed by a time-variable sequence of a plurality of individual quality criteria comprising at least one of an input signal amplitude, a signal-to-noise ratio, a jitter amplitude, a spectral distribution of the signals, a frame error rate, and a bit error rate.

7. The device according to claim 1, wherein the transmission means, transmission conductor arrangement, receiving means, and receiving coupler arrangement are configured to transmit optical signals.

8. The device according to claim 1, wherein the transmission means, transmission conductor arrangement, receiving means, and receiving coupler arrangement are configured to transmit electrical signals.

9. The device according to claim 1, wherein the transmission conductor arrangement is divided into a plurality of segments, and the receiving coupler arrangement has at least one coupler more than the number of segments of the transmission conductor arrangement.

10. The device according to claim 1, wherein a buffer memory is provided for intermediate storage of received data.

11. The device according to claim 1, wherein data received more than once are rejected.

12. The device according to claim 1, wherein the transmission conductor arrangement is divided into a plurality of segments, individual segments being fed with signals by the transmission means in such a way that optionally bit clock pulses or frame clock pulses of adjacent segments are almost in phase with one another.

13. The device according to claim 1, wherein at least one data channel having a relatively low data rate is multiplexed with a data stream.

14. A computer tomograph comprising a device for transmitting data between a first part and a second part of the computer tomograph, the parts being rotatable relative to each other, in which the first part comprises:
   at least one data source;
   at least one transmission means for receiving data from the data source and transmitting signals; and
   a transmission conductor arrangement which is fed by the transmission means for guiding the signals along at least a predetermined region of the first part;
   and the second part comprises:
   a receiving coupler arrangement for tapping signals from the transmission conductor arrangement;
   at least one receiving means for receiving signals from the receiving coupler arrangement;
   a data sink for evaluating or further processing the data supplied by the receiving means;
   wherein the receiving coupler arrangement includes at least two couplers, at least one coupler being engaged with the transmission conductor arrangement at any moment during a transmission; and
   wherein the receiving means comprises at least two receivers, each connected to at least one coupler, and also an evaluation means for evaluating signals from the receivers, and the evaluation means selects, on the basis of at least one predetermined quality criterion of the signals from the receivers, the data from at least one receiver for forwarding to the data sink.

* * * * *